United States Patent [19]

Shih et al.

[11] Patent Number: 5,498,743

[45] Date of Patent: Mar. 12, 1996

[54] PROCESS FOR PRODUCING DIALKYLCARBONATES

[75] Inventors: Stuart S. Shih, Cherry Hill; Margaret M. Wu, Skillman, both of N.J.; Tsoung Y. Yan, Philadelphia, Pa.

[73] Assignee: Mobil Oil Corp., Fairfax, Va.

[21] Appl. No.: 325,919

[22] Filed: Oct. 20, 1994

[51] Int. Cl.$^6$ .................................................. C07C 69/96
[52] U.S. Cl. .................................................... 558/277
[58] Field of Search .............................................. 558/277

[56] References Cited

U.S. PATENT DOCUMENTS

| | | | |
|---|---|---|---|
| 3,896,090 | 7/1975 | Maximovich | 260/77.5 D |
| 4,062,884 | 12/1977 | Romano et al. | 260/463 |
| 4,181,676 | 1/1980 | Buysch et al. | 260/463 |
| 4,434,105 | 2/1984 | Buysch et al. | 260/463 |
| 4,652,667 | 3/1987 | Green | 558/277 |
| 4,691,041 | 9/1987 | Duranleau et al. | 558/277 |
| 4,891,421 | 1/1990 | Nishimura et al. | 528/370 |
| 5,118,818 | 6/1992 | Delledonne et al. | 549/230 |
| 5,173,518 | 12/1992 | Bott et al. | 521/172 |
| 5,231,212 | 7/1993 | Buysch et al. | 558/277 |
| 5,235,087 | 8/1993 | Klausener et al. | 558/260 |
| 5,252,771 | 10/1993 | Harley et al. | 558/274 |
| 5,283,351 | 2/1994 | Kezuka et al. | 558/260 |

Primary Examiner—José G. Dees
Assistant Examiner—Dwayne C. Jones
Attorney, Agent, or Firm—Alexander J. McKillop; Dennis P. Santini

[57] ABSTRACT

A process is provided for synthesis of dialkylcarbonate, e.g., dimethylcarbonate, by reacting an alcohol, e.g., methanol, with a cyclic carbonate, e.g., propylene carbonate, in the presence of a catalyst comprising an alkaline earth metal halide, e.g., magnesium iodide, and a solid support having a high surface area and controlled surface hydroxyl concentration.

22 Claims, No Drawings

PROCESS FOR PRODUCING DIALKYLCARBONATES

FIELD OF THE INVENTION

This invention relates to a process for synthesis of dialkylcarbonates by reacting a certain alcohol with a cyclic carbonate having the formula

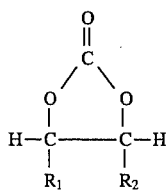

wherein $R_1$ and $R_2$ are selected from the group consisting of hydrogen, alkyl of from 1 to 10 carbon atoms, alkoxy of from 1 to 5 carbon atoms, and combinations thereof, in the presence of a catalyst comprising an alkaline earth metal halide and a particular solid support having a high surface area and controlled surface hydroxyl concentration.

BACKGROUND OF THE INVENTION

Reaction of alcohols and cyclic carbonates, such as those of the above formula, to produce alkylcarbonates by transesterification in the presence of various catalysts is known in the art. For example, U.S. Pat. No. 3,896,090 discloses a process for preparing polycarbonates from carbon dioxide and 1,2-epoxides or from alkylene carbonates and a monomeric polyol in the presence of alkali metal borate, alkaline earth metal borate, ammonium borate, or hydrocarbyloxy titanate catalyst. Also, U.S. Pat. No. 4,691,041 teaches a process for the preparation of ethylene glycol and dimethylcarbonate by reacting methanol and ethylene carbonate in the presence of a series of heterogenous catalyst systems including ion exchange resins with tertiary amine, quaternary ammonium, sulfonic acid and carboxylic acid functional groups, alkali and alkaline earth silicates impregnated into silica and ammonium exchanged zeolites.

U.S. Pat. No. 4,181,676 discloses use of alkali metal and/or alkali metal compound catalyst for the preparation of a dialkylcarbonate by contacting a glycol carbonate with alcohol at an elevated temperature in the presence of less than 0.01 percent by weight of the alkali metal or alkali metal compound. A list of some conventional transesterification catalysts was published in U.S. Pat. No. 5,173,518, including tetraisopropyl orthotitanate, dibutyltin oxide, dibutyltin dilaurate and zirconium (IV) acetyl-acetonate, and alkali metal alkoxides, for example sodium methoxide, sodium ethoxide, and potassium ethoxide.

A list of catalysts for esterification or ester-interchange is shown in U.S. Pat. No. 4,891,421, including inorganic acids and organic acids; chlorides, oxides, and hydroxides of metals such as Li, Na, K, Rb, Ca, Mg, Sr, Zn, Al, Ti, V, Cr, Mn, Fe, Co, Ni, Cu, Zr, Pd, Sn, Sb, and Pb; salts of the above-exemplified metals with fatty acids such as acetic acid, oxalic acid, octylic acid, laurie acid, and naphthenic acid; alcoholates such as sodium methylate, sodium ethylate, aluminum triisopropoxide, isopropyl titanate, n-butyl titanate, and octyl titanate; phenolates such as sodium phenolate; and organic metal compounds of metals such as Al, Ti, Zn, Sn, Zr, and Pb.

U.S. Pat. No. 4,062,884 discloses a process for the preparation of dialkylcarbonates by reacting an alcohol with a cyclic carbonate, wherein the reaction is carried out in the presence of an organic base catalyst, preferably a tertiary aliphatic amine.

Aluminum trifluoride catalyst is used in U.S. Pat. No. 5,252,771 in a process for the production of a diarylcarbonate useful in the preparation of polycarbonate molding resins comprising contacting an aromatic hydroxy compound and a carbonyl halide or aryl haloformate. The support for the aluminum trifluoride catalyst in this process includes refractory oxides, ceramics, or other inert materials such as silica, aluminosilicate, carbon, silicon carbide, aluminum nitride, titania, high silica ZSM-5, and zirconia.

Thallium is claimed as a catalyst in U.S. Pat. No. 4,434,105 for a process for preparing a dialkylcarbonate which comprises contacting an alkylene oxide with an aliphatic or cycloaliphatic alcohol and carbon dioxide at an elevated temperature. This patent lists various catalysts useful for such a conversion reaction including basic organic nitrogen compounds and oxides, hydroxides, and salts of alkali and alkaline earth metals. Solid supports are mentioned for the catalyst useful in the latter process such as magnesia and alumina.

Dialkylcarbonates can be prepared in a continuous manner by transesterification of ethylene carbonate or propylene carbonate with alcohols in the presence of a catalyst in a column equipped with packing or baffles in U.S. Pat. No. 5,231,212 by passing the reactants in countercurrent such that the ethylene carbonate or propylene carbonate is metered into the upper part of the column, the alcohol is metered into the lower part of the column, and the catalyst is arranged as a fixed bed in the column or is also metered into the upper part of the column in solution or suspension. A variety of catalysts are taught for use in the patent process, including hydrides, oxides, hydroxides, alcoholates, amides, or salts of alkali metals, preferably lithium, sodium, and potassium. Thallium compounds, nitrogen-containing bases, heterogeneous catalysts, complexes or salts of tin, titanium, or zirconium, and bifunctional organic catalysts are also suggested for the patent process.

U.S. Pat. No. 5,235,087 discloses manufacture of dialkylcarbonates by reacting carbon monoxide with alkyl nitrites over a modified platinum metal-supported catalyst at an elevated temperature in a continuous gas phase reaction, the reaction being carried out with the exclusion of additional oxidizing substances and, optionally, the presence of a lower alcohol.

In a similar vein, U.S. Pat. No. 5,283,351 discloses a process for producing an organic carbonate which comprises reacting an organic hydroxy compound and carbon monoxide in the absence of oxygen and in the presence of a catalyst comprising (a) palladium or a palladium compound, (b) a quinone or an aromatic diol formed by reduction of the quinone or a mixture thereof, and (c) a halogenated onium compound. The palladium component may be deposited on carbon, alumina, silica, silica-alumina, or zeolite.

Cyclic amidine catalyst is disclosed for a process for the transesterification of carbonate esters and carboxylic acid esters at elevated temperatures in U.S. Pat. No. 4,652,667. The amidine catalyst can be homogeneous or heterogeneous. In the heterogeneous catalyst, the amidine compound is chemically bonded to an inert support through the bonding of the surface atoms of the support to one or more of the free valences of the amidine group. Suitable supports include organic supports such as polymer resins, e.g., polystyrene, polystyrene/divinyl benzene copolymer, polyacrylate, and polypropylene; or inorganic supports such as silica, alumina, silica-alumina, clay, zirconia, titania, hafnia, carbides, diatomaceous earth, and zeolites.

SUMMARY OF THE INVENTION

This invention relates to a process for synthesis of dialkylcarbonates, e.g., dimethylcarbonate, by reacting a certain alcohol, e.g., methanol, with a cyclic carbonate having the formula

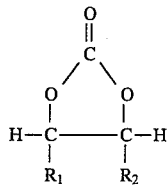

wherein $R_1$ and $R_2$ are selected from the group consisting of hydrogen, alkyl of from 1 to 10 carbon atoms, alkoxy of from 1 to 5 carbon atoms, and combinations thereof, in the presence of a catalyst comprising an alkaline earth metal halide, e.g., magnesium iodide, and a particular solid support, such as, for example, silica, MCM-41 or pillared layered material, having a high surface area of greater than about 10 m²/g, for example from about 50 m²/g to about 1000 m²/g, preferably from about 100 m²/g to about 600 m²/g, and controlled surface hydroxyl concentration of from about 0.1 to about 5.0 m mole/g, preferably from about 0.2 to about 3.0 m mole/g.

The present process provides improved selectivity to desired product, e.g., dimethylcarbonate, and the required catalyst is easier to handle and less corrosive than conventional homogeneous catalysts.

DESCRIPTION OF SPECIFIC EMBODIMENTS

The carbonates manufactured by the present process are important intermediates for the synthesis of fine chemicals, pharmaceuticals, and plastics. For example, the dimethylcarbonate hereby synthesized is useful as a substitute for phosgene as a carbonylation agent or for dimethylsulfate as a methylating agent in fine chemicals production. Light dialkylcarbonate products of this invention such as dimethylcarbonate and diethylcarbonate are potential gasoline oxygenates because of their high octanes (R+O =104 and 107, respectively) and high oxygen contents (53.3 and 40.7 wt. %, respectively). For comparison, methyltert-butylether (MTBE), a well-known gasoline blending agent, has a blending octane of 100 (R+O) and an oxygen content of 18 wt. %. Therefore, in order for a gasoline blend to have a target 2.7% oxygen, the blend would have to contain 14.7 vol. % MTBE, and only 3.6 vol. % dimethylcarbonate or 5.1 vol. % diethylcarbonate. Also, higher dialkylcarbonate products of this invention such as, for example, dinonylcarbonate, can be used as blending components for diesel fuel to improve combustion properties.

The present process involves transesterification of alkylene carbonate with an alcohol. In general, the reaction of the invention may be depicted as follows:

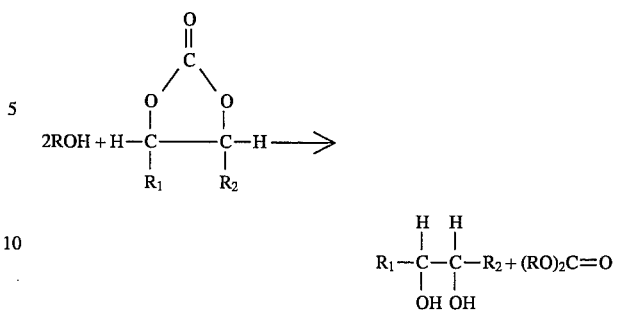

wherein R is selected from the group consisting of alkyl of from 1 to 10 carbon atoms, such as, for example alkyl of from 1 to 5 carbon atoms, e.g., methyl, ethyl, propyl, and butyl, and mixtures thereof; and $R_1$ and $R_2$ are selected from the group consisting of hydrogen, alkyl of from 1 to 10 carbon atoms, e.g., methyl, ethyl, hexyl, and nonyl, alkoxy of from 1 to 5 carbon atoms, e.g., methoxy and ethoxy, and combinations thereof.

Examples of the present process include (1) reaction of methanol with propylene carbonate to produce dimethylcarbonate and propylene glycol; (2) reaction of methanol with ethylene carbonate to produce dimethylcarbonate and ethylene glycol; and (3) reaction of ethanol with propylene carbonate to produce diethylcarbonate and propylene glycol. In each case the reaction selectivity is toward the dialkylcarbonate in high yield.

The present process may be conducted in a fixed bed of catalyst, thereby improving conversion and selectivity by, for example, reducing back mixing which may occur in a typical stirred-tank reactor which uses a homogeneous catalyst.

Reaction conditions required for the present process include a temperature of from about 50° C. to about 300° C., preferably from about 100° C. to about 200° C.; a pressure of from about 50 psig to about 2000 psig, preferably from about 100 psig to about 1000 psig; and a liquid hourly space velocity of from about 0.1 hr$^{-1}$ to about 10 hr$^{-1}$, preferably from about 0.5 hr$^{-1}$ to about 5 hr$^{-1}$.

The catalyst for use herein is an alkaline earth metal halide supported on a particular, stable, solid support having a high surface hydroxyl concentration. The alkaline earth metal may be, for example, magnesium, calcium, strontium, or combination thereof, with magnesium preferred. The halide may be, for example, chloride, bromide, iodide, or combination thereof, with iodide preferred. The amount of alkaline earth metal halide on the solid support will be at least about 0.6 m mole/gram of support, preferably from about 1.0 m mole/gram to about 3.0 m mole/gram.

The solid support material must be stable at conditions of reaction and will have a surface area of greater than about 10 m²/g for example from about 50 m²/g to about 1000 m²/g, preferably from about 100 m²/g to about 600 m²/g. The support material will have a controlled surface hydroxyl concentration of from about 0.1 m mole/g to about 5.0 m mole/g, preferably from about 0.2 m mole/g to about 3.0 m mole/g.

Surface hydroxyl concentration of such a support may be controlled by treating the support with basic solution (e.g., ion-exchanging the support), hydrothermal treating (e.g., steaming), and/or programmed temperature calcination.

Examples of solid supports useful herein if satisfying the surface hydroxyl concentration requirement include silica, synthetic mesoporous crystalline material, e.g., MCM-41 or MCM-48, and certain clay or pillared, layered material.

Mesoporous crystalline materials are taught in U.S. Pat. Nos. 5,098,684; 5,102,643; and 5,198,203, each incorporated herein by reference. One such material useful as the solid catalyst support in this process is MCM-41 of U.S. Pat. No. 5,098,684. MCM-41 is a synthetic composition of matter comprising an inorganic, porous, non-layered phase having a hexagonal arrangement of uniformly-sized pores with a maximum perpendicular cross-section pore dimension of at least about 13 Angstroms, and within the range of from about -13 Angstroms to about 200 Angstroms. This novel crystalline composition exhibits a hexagonal electron diffraction pattern that can be indexed with a $d_{100}$ value greater than about 18 Angstroms, and a benzene adsorption capacity of greater than about 15 grams benzene/100 grams crystal at 50 torr and 25° C.

MCM-41 may be distinguished from other porous, inorganic solids by the regularity of its large, open pores, whose pore size more nearly resembles that of amorphous or para-crystalline materials, but whose regular arrangement and uniformity of size (pore size distribution within a single phase of, for example, ±25%, usually ±15% or less of the average pore size of that phase) resemble more those of crystalline framework materials such as zeolites. The material appears to have a hexagonal arrangement of large, open channels that can be synthesized with open internal diameters from about 13 Angstroms to about 200 Angstroms. The term "hexagonal" is intended to encompass not only materials that exhibit mathematically perfect hexagonal symmetry within the limits of experimental measurement, but also those with significant observable deviations from that ideal state. A working definition as applied to the microstructure of MCM-41 would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as ±25% random deviation from the average repeat distance between adjacent channels sill clearly give recognizable images of MCM-41. Comparable variations are also observed in the $d_{100}$ values from the electron diffraction patterns.

The most regular preparations of MCM-41 give an X-ray diffraction pattern with a few distinct maxima in the extreme low-angle region. The positions of these peaks approximately fit the positions of the hkO reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low-angle region of the X-ray diffraction pattern have been found to contain substantial amounts of the material in them. Other techniques to illustrate the microstructure of this material are transmission electron microscopy and electron diffraction. Properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hkO projection of the hexagonal lattice and is related to the repeat distance $a_o$ between channels observed in the electron micrographs through the formula $d_{100}=a_o z \sqrt{3}/2$. This $d_{100}$ spacing observed in the electron diffraction patterns corresponds to the d-spacing of a low-angle peak in the X-ray diffraction pattern of the material. The most highly ordered preparations of MCM-41 have 20–40 distinct spots observable in the electron diffraction patterns. These patterns can be indexed with the hexagonal hkO subset of unique reflections of 100, 110, 200, 210, etc., and their symmetry-related reflections.

In its calcined form, MCM-41 may be further characterized by an X-ray diffraction pattern with at least one peak at a position greater than about 18 Angstrom units d-spacing (4.909 degrees two-theta for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to ensure no pore blockage by incidental contaminants, if necessary).

More particularly, calcined crystalline non-layered MCM-41 may be characterized by an X-ray diffraction pattern with at least two peaks at positions greater than about 10 Angstrom units d-spacing (8.842 degrees two-theta for Cu K-alpha radiation), at least one of which is at a position greater than about 18 Angstrom units d-spacing, and no peaks at positions less than about 10 Angstrom units d-spacing with relative intensity greater than about 20% of the strongest peak. Still more particularly, the X-ray diffraction pattern of calcined MCM-41 will have no peaks at positions less than about 10 Angstrom units d-spacing with relative intensity greater than about 10% of the strongest peak. In any event, at least one peak in the X-ray diffraction pattern will have a d-spacing that corresponds to the $d_{100}$ value of the electron diffraction pattern of the material.

Synthesis and treatment of MCM-41 for use herein are detailed in U.S. Pat. No. 5,098,684, as well as U.S. Pat. Nos. 5,108,725; 5,156,829; 5,104,515; 5,112,589; 5,110,572; 5,145,816; 5,156,828; 5,215,737; and 5,211,934, each expressly incorporated herein by reference.

Another material useful as the solid catalyst support in this process is MCM-48 of U.S. Pat. No. 5,198,203. MCM-48 is a synthetic composition of matter comprising an inorganic, porous, non-layered phase which may have uniformly-sized pores with a pore dimension of at least about 13 Angstroms, and within the range of from about 13 Angstroms to about 200 Angstroms as measured by argon physisorption. This novel crystalline composition exhibits an X-ray diffraction pattern and a benzene adsorption capacity usually greater than about 10 grams benzene/100 grams crystal at 50 torr and 25° C.

MCM-48 may be distinguished from other porous, inorganic solids by the regularity of its' large, open pores, whose pore size more nearly resembles that of amorphous or para-crystalline materials, but whose regular arrangement and uniformity of size (pore size distribution within a single phase of, for example, −25%, usually ±15% or less of the average pore size of that phase) resemble more those of crystalline framework materials such as zeolites. The material appears to have a regular arrangement of large, open pores that can be synthesized with open, internal dimensions from about 13 Angstroms to about 200 Angstroms.

The most regular preparations of MCM-48, following removal of organic, e.g., by calcination at 540° C. in air for at least about one hour, give an X-ray diffraction pattern with distinct maxima in the extreme low-angle region. The positions of these peaks will vary somewhat with changes in the pore diameters of the materials, but the ratios of d-spacings of those peaks will remain fixed. Using $d_1$ to indicate the d-spacings of the strongest peak in the X-ray diffraction pattern (relative intensity =100), the X-ray diffraction pattern of the calcined material of the present invention exhibits $d_1$ at a position greater than about 18 Angstroms d-spacing and at least one additional weaker peak with d-spacing $d_2$ such that the ratios of these d-spacings relative to $d_1$, i.e., $d_n/d_1$, correspond to the ranges given in Table 1.

TABLE 1

| d-Spacing, $d_n$, Angstroms | $d_n/d_1$ | Relative Intensity |
|---|---|---|
| $d_1$, > ~ 18 | 1.0 | 100 |
| $d_2$ | 0.87 ± 0.06 | w–m |

More particularly, the X-ray diffraction pattern of the calcined MCM-48 includes at least two additional weaker peaks at d-spacings $d_2$ and $d_3$ such that the ratios of these d-spacings relative to the strongest peak $d_1$ (at a position greater than about 18 Angstroms d-spacing) correspond to the ranges given in Table 2.

TABLE 2

| d-Spacing, $d_n$, Angstroms | $d_n/d_1$ | Relative Intensity |
|---|---|---|
| $d_1$, > ~ 18 | 1.0 | 100 |
| $d_2$ | 0.87 ± 0.06 | w–m |
| $d_3$ | 0.52 ± 0.04 | w |

Still more particularly, the X-ray diffraction pattern of the calcined MCM-48 includes at least four additional weaker peaks at d-spacings $d_2$, $d_3$, $d_4$, and $d_5$ such that the ratios of these d-spacings relative to the strongest peak $d_1$ (at a position greater than about 18 Angstroms d-spacing) correspond to the ranges given in Table 3.

TABLE 3

| d-Spacing, $d_n$, Angstroms | $d_n/d_1$ | Relative Intensity |
|---|---|---|
| $d_1$, > ~ 18 | 1.0 | 100 |
| $d_2$ | 0.87 ± 0.06 | w–m |
| $d_3$ | 0.55 ± 0.02 | w |
| $d_4$ | 0.52 ± 0.01 | w |
| $d_5$ | 0.50 ± 0.01 | w |

In its calcined form crystalline MCM-48 may be further characterized by an equilibrium benzene adsorption capacity usually greater than about 10 grams benzene/100 grams crystal at 50 torr and 25° C. (basis: crystal material having been treated in an attempt to ensure no pore blockage by incidental contaminants, if necessary).

Synthesis and treatment of MCM-48 for use herein are detailed, for example, in U.S. Pat. No. 5,198,203; 5,104,515; 5,112,589; 5,145,816; and 5,300,277, each expressly incorporated herein by reference.

The equilibrium benzene adsorption capacity characteristics of the mesoporous crystalline materials MCM-41 and MCM-48 are measured on the basis of no pore blockage by incidental contaminants. For instance, the sorption test will be conducted on the crystalline material phase having any pore blockage contaminants and water removed by ordinary methods. Water may be removed by dehydration techniques, e.g., thermal treatment. Pore-blocking, inorganic, amorphous materials, e.g., silica, and organic may be removed by contact with acid or base or other chemical agents such that the detrital material will be removed without detrimental effect on the crystal structure. For example, the equilibrium benzene adsorption capacities referred to above are determined by contacting the solid material, after dehydration or calcination at, for example, about 540° C. for at least about one hour, e.g., about six hours, and other treatment, if necessary, in an attempt to remove any pore blocking contaminants, at 25° C. and 50 torr benzene until equilibrium is reached. The weight of benzene sorbed is then determined.

The calcined, inorganic, non-layered, crystalline MCM-41 and MCM-48 are characterized as having a pore size of about 13 Angstroms or greater, e.g., 15 Angstroms or greater, as measured by physisorption measurements. Pore size is considered a maximum perpendicular cross-section pore dimension of the crystal.

X-ray diffraction data referred to above for MCM-41 and MCM-48 were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3, and 0.2 mm, respectively. Different slit systems may produce differing intensities for the peaks. The mesoporous crystalline materials that have the largest pore sizes may require more highly collimated incident X-ray beams in order to resolve the low angle peak from the transmitted incident X-ray beam.

The diffraction data were recorded by step-scanning at 0.04 degrees of two-theta, where theta is the Bragg angle, and a counting time of 10 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine. Overlap between peaks required the use of deconvolution techniques to determine peak positions in many cases. The intensities were uncorrected for Lorentz and polarization effects.

Another useful solid catalyst support for use herein is pillared layered material.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648, and include layered silicates, magadiite, kenyaite, trititanates, and perovskites. Another example of a non-water swellable layered material, which can be swollen with certain organic swelling agents, is described in U.S. Pat. No. 4,831,006.

Once a layered material is swollen, the material may be pillared by interposing a thermally stable substance, such as silica, between the spaced-apart layers. The aforementioned U.S. Pat. Nos. 4,831,006 and 4,859,648 describe methods for pillaring the non-water swellable-layered materials described therein and are expressly incorporated herein by reference for definition of pillaring and pillared materials.

Other patents teaching pillaring of layered materials and the pillared products include U.S. Pat. Nos. 4,216,188;

4,248,739; 4,176,090; and 4,367,163; and European Patent Application 205,711.

A non-limiting example of silica useful herein as the solid catalyst support is silica gel. Clays useful as the solid catalyst support for the present process include montmorillonite.

In order to more fully illustrate the nature of the present invention and the manner of practicing same, the following examples are presented.

EXAMPLE 1

A 20 gram quantity of silica gel (Davisil 646) with surface area of 300 m²/g, surface hydroxyl concentration of 0.4 m mole/g, pore volume of 1.15 cc/g, particle size of 35–60 mesh, and calcined at 600° C. for 16 hours in air was slurried in about 50 cc dried diethyl ether solvent in a reactor flask under nitrogen atmosphere. Then a 4 cc solution of methylmagnesium iodide in diethyl ether was added slowly into the slurry. A large amount of gas was evolved. After two hours of reaction at room temperature, diethyl ether solvent was removed by purging nitrogen through the flask. Any residual solvent was further removed by drying at high vacuum for 16 hours. The resulting free-flowing catalyst was stored inside a glove box with less than 1 ppm of water and oxygen until use. The catalyst contained a theoretical amount of 0.6 m mole MgI per gram of silica.

EXAMPLE 2

The preparation of Example 1 was repeated, except that 10 cc of the methylmagnesium iodide solution was added to a silica gel based on Davisil 635 with 480 m²/g surface area, 0.6 m mole/g surface hydroxyl concentration, 0.75 cc/g pore volume, 60–100 mesh size material calcined at 300° C. in air for 16 hours. The catalyst product contained a theoretical amount of 1.5 m mole MgI per gram of silica.

EXAMPLE 3

For comparison purposes, the preparation procedure of Example 1 was repeated, except that dried pentane solvent was used to slurry the catalyst and 3.3 cc of titanium tetraisoproxide was used in the preparation. The catalyst product of this example contained a theoretical amount of 0.6 m mole Ti(OP)$_3$ per gram of silica.

EXAMPLE 4

For comparison purposes, a Tl$_2$CO$_3$/4A catalyst was prepared by first crushing Linde 4A sieve to 20–40 mesh size. Then 2 grams of Tl$_2$CO$_3$ was dissolved in 16 cc warm water. The Tl$_2$CO$_3$ solution was then mixed with 20 grams of the 4A sieve, and the resulting solid product was dried at 110° C. overnight.

EXAMPLE 5

Each catalyst prepared above was evaluated in an up-flow, fixed-bed reactor operating at 1.0 hr⁻¹ LHSV and 100 psig pressure. Feedstock used in the experiments consisted of methanol (MeOH) and propylene carbonate (PC) in a 4/1 MeOH/PC mole ratio. When the catalyst was that of Example 4, NaI was dissolved in the feedstock to an amount of 1 wt. %. Results of these experiments are presented in Table 4.

TABLE 4

| Catalyst of Example | 1 | | 2 | | 3 | | 4 | |
|---|---|---|---|---|---|---|---|---|
| Temp, °C. | 130 | 150 | 130 | 150 | 130 | 150 | 130 | 150 |
| PC Conversion, % | 7.2 | 16.6 | 31.3 | 41.8 | 2.3 | 5.0 | 34.4 | 39.0 |
| Selectivity, mole ratio (based on PC converted) | | | | | | | | |
| Dimethylcarbonate | 0.79 | 0.92 | 0.92 | 0.91 | 0.49 | 0.55 | 0.93 | 0.59 |
| Propylene Glycol | 0.98 | 1.00 | 1.00 | 1.00 | 0.93 | 0.87 | 1.00 | 0.63 |

As shown by these results, the present process using catalyst of Example 1 with 0.6 m mole MgI/gram of silica is significantly better than using catalyst of Example 3 with 0.6 m mole Ti(OPr)$_3$/gram of silica. By this comparison, the present process provided higher propylene carbonate conversion at each experiment temperature and higher dimethylcarbonate and propylene glycol selectivities.

Further, the present process using catalyst of Example 2 with 1.5 m mole MgI/gram of silica provided higher selectivities for dimethylcarbonate and propylene glycol compared to use of catalyst of Example 4 with NaI, while propylene carbonate conversions at both reaction temperatures remained comparable.

We claim:

1. A process for synthesis of dialkylcarbonate which comprises reacting an alcohol of the formula ROH, wherein R is alkyl of from 1 to 10 carbon atoms or mixtures thereof, with a cyclic carbonate of the formula

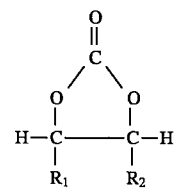

wherein R$_1$ and R$_2$ are hydrogen, alkyl of from 1 to 10 carbon atoms, alkoxy of from 1 to 5 carboll atoms, or a combination thereof, in the presence of a catalyst comprising an alkaline earth metal halide supported on a solid support having a surface area of greater than about 10 m²/g and a surface hydroxyl concentration of from about 0.1 m mole/g to about 5.0 m mole/g, at reaction conditions including a temperature of from about 50° C. to about 300° C., a pressure of from about 50 psig to about 2000 psig and a liquid hourly space velocity of from about 0.1 hr⁻¹ to about 10 hr⁻¹ to provide a product comprising (RO)$_2$C=0.

2. The process of claim 1 wherein R is alkyl of from 1 to 5 carbon atoms, and R$_1$ and R$_2$ are hydrogen, methyl, or a combination thereof.

3. The process of claim 1 wherein R is methyl, R$_1$ is hydrogen, and R$_2$ is methyl.

4. The process of claim 1 wherein said alkaline earth metal comprises magnesium, calcium, strontium, or a combination thereof; and said halide comprises chloride, bromide, iodide, or a combination thereof.

5. The process of claim 1 wherein said solid support comprises silica, synthetic mesoporous crystalline material, clay, or pillared layered material.

6. The process of claim 1 wherein said solid support comprises silica.

7. The process of claim 1 wherein said solid support comprises a synthetic mesoporous crystalline material.

8. The process of claim 7 wherein said mesoporous material comprises MCM-41 or MCM-48.

9. The process of claim 1 wherein said catalyst comprises magnesium iodide supported on silica.

10. The process of claim 1 wherein said reaction conditions include a temperature of from about 100° C. to about 200° C., a pressure of from about 100 psig to about 1000 psig, and a liquid hourly space velocity of from about 0.5 hr$^{-1}$ to about 5 hr$^{-1}$.

11. The process of claim 1 wherein said catalyst comprises at least about 0.6 m mole alkaline earth metal halide/gram of support.

12. The process of claim 11 wherein said catalyst comprises from about 1.0 to about 3.0 m mole alkaline earth metal halide/gram of support.

13. A process for synthesis of dimethylcarbonate which comprises reacting methanol with propylene carbonate in the presence of a catalyst comprising an alkaline earth metal halide supported on a solid support having a surface area of greater than about 10 m$^2$/g and a surface hydroxyl concentration of from about 0.1 m mole/g to about 3.0 m mole/g at reaction conditions including a temperature of from about 50° C. to about 300° C., a pressure of from about 50 psig to about 2000 psig and a liquid hourly space velocity of from about 0.1 hr$^{-1}$ to about 10 hr$^{-1}$.

14. The process of claim 13 wherein said alkaline earth metal comprises magnesium, calcium, strontium, or a combination thereof; and said halide comprises chloride, bromide, iodide, or a combination thereof.

15. The process of claim 13 wherein said solid support comprises silica, synthetic mesoporous crystalline material, clay, or pillared layered material.

16. The process of claim 13 wherein said solid support comprises silica.

17. The process of claim 13 wherein said solid support comprises a synthetic mesoporous crystalline material.

18. The process of claim 17 wherein said mesoporous material comprises MCM-41 or MCM-48.

19. The process of claim 13 wherein said catalyst comprises magnesium iodide supported on silica.

20. The process of claim 13 wherein said reaction conditions include a temperature of from about 100° C. to about 200° C., a pressure of from about 100 psig to about 1000 psig, and a liquid hourly space velocity of from about 0.5 hr$^{-1}$ to about 5 hr$^{-1}$.

21. The process of claim 13 wherein said catalyst comprises at least about 0.6 m mole alkaline earth metal halide/gram of support.

22. The process of claim 21 wherein said catalyst comprises from about 1.0 to about 3.0 m mole alkaline earth metal halide/gram of support.

* * * * *